(12) United States Patent
Melsheimer

(10) Patent No.: US 7,497,872 B2
(45) Date of Patent: Mar. 3, 2009

(54) RETAINER FOR A STENT-GRAFT

(75) Inventor: Jeffry S. Melsheimer, Lafayette, IN (US)

(73) Assignee: Cook Incorporated, Bloomington, IN (US)

( * ) Notice: Subject to any disclaimer, the term of this patent is extended or adjusted under 35 U.S.C. 154(b) by 790 days.

(21) Appl. No.: 10/795,641

(22) Filed: Mar. 8, 2004

(65) Prior Publication Data

US 2005/0209679 A1     Sep. 22, 2005

(51) Int. Cl.
*A61F 2/06* (2006.01)
(52) U.S. Cl. ..................................... 623/1.13
(58) Field of Classification Search ............... 623/1.13, 623/1.15, 1.14, 1.16, 1.18, 1.2
See application file for complete search history.

(56) References Cited

U.S. PATENT DOCUMENTS

| | | | |
|---|---|---|---|
| 5,211,658 A | 5/1993 | Clouse | ............ 623/1 |
| 5,667,523 A | 9/1997 | Bynon et al. | |
| 5,843,166 A | 12/1998 | Lentz et al. | |
| 5,865,723 A * | 2/1999 | Love | ............ 600/36 |
| 6,053,943 A | 4/2000 | Edwin et al. | |
| 6,099,559 A * | 8/2000 | Nolting | ............ 623/1.16 |
| 6,168,619 B1 | 1/2001 | Dinh et al. | |
| 6,214,040 B1 | 4/2001 | Jayaraman | |
| 6,296,661 B1 | 10/2001 | Davila et al. | |
| 6,312,458 B1 | 11/2001 | Golds | |
| 6,319,277 B1 | 11/2001 | Rudnick et al. | |
| 6,325,820 B1 | 12/2001 | Khosravi et al. | |
| 6,371,980 B1 * | 4/2002 | Rudakov et al. | ............ 623/1.12 |
| 6,520,984 B1 | 2/2003 | Garrison et al. | ............ 623/1.11 |
| 6,547,814 B2 | 4/2003 | Edwin et al. | |
| 6,579,307 B2 | 6/2003 | Sarac | |
| 6,579,314 B1 | 6/2003 | Lombardi et al. | |
| 6,699,277 B1 * | 3/2004 | Freidberg et al. | ............ 623/1.13 |
| 7,189,255 B2 * | 3/2007 | DePalma | ............ 623/1.13 |
| 2003/0120332 A1 | 6/2003 | Hartley | |
| 2003/0139797 A1 * | 7/2003 | Johnson et al. | ............ 623/1.13 |
| 2003/0171800 A1 | 9/2003 | Bicek et al. | |
| 2003/0176911 A1 | 9/2003 | Iancea et al. | |

FOREIGN PATENT DOCUMENTS

| | | |
|---|---|---|
| EP | 0 960 607 A1 | 12/1999 |
| EP | 1 330 993 A1 | 7/2003 |
| WO | WO 01/66035 A2 | 9/2001 |
| WO | WO 2004/047687 A1 | 6/2004 |

OTHER PUBLICATIONS

International Search Report from corresponding PCT Application No. PCT/US2005/007077, dated Jul. 12, 2005, 5 pages.

* cited by examiner

*Primary Examiner*—Todd E Manahan
*Assistant Examiner*—Ryan Severson
(74) *Attorney, Agent, or Firm*—Brinks Hofer Gilson & Lione

(57) ABSTRACT

A stent assembly includes a stent, a graft material and a retainer. The graft material is secured between the stent and the retainer by retaining members on the retainer and complimentary receiver regions on the stent. In order to secure the graft material, the retainer is oriented relative to the stent so that the retaining members align with the receiver regions. The orientation of the retainer relative to the stent allows the retaining members to cooperate with the receiver regions. As a result, the graft material is secured against the stent without perforating the graft material.

23 Claims, 7 Drawing Sheets

RETAINER FOR A STENT-GRAFT

BACKGROUND

The present invention relates generally to medical devices and particularly to a stent with a graft retained against the stent.

Although stent graft assemblies may be used to treat a number of medical conditions, one common use of stent graft assemblies relates to the treatment of aneurysms. As those in the art well know, an aneurysm is an abnormal widening or ballooning of a portion of an artery. Generally, this condition is caused by a weakness in the blood vessel wall. High blood pressure and atherosclerotic disease may also contribute to the formation of aneurysms. Aneurysms may form in blood vessels throughout the vasculature. However, common types of aneurysms include aortic aneurysms, cerebral aneurysms, popliteal artery aneurysms, mesenteric artery aneurysms, and splenic artery aneurysms. If not treated, an aneurysm may eventually rupture, resulting in internal hemorrhaging. In many cases, the internal bleeding is so massive that a patient can die within minutes of an aneurysm rupture. For example, in the case of aortic aneurysms, the survival rate after a rupture can be as low as 20%.

Traditionally, aneurysms have been treated with surgery. For example, in the case of an abdominal aortic aneurysm, the abdomen is opened surgically and the widened section of the aorta is removed. The remaining ends of the aorta are then surgically reconnected. In certain situations the surgeon may choose to replace the excised section of the aorta with a graft material such as Dacron, instead of directly reconnecting the two ends of the blood vessel together. In still other situations, the surgeon may put a clip on the blood vessel at the neck of the aneurysm between the aneurysm and the primary passageway of the vessel. The clip then prevents blood flow from the vessel from entering the aneurysm.

An alternative to traditional surgery is endovascular treatment of the blood vessel with a stent-graft. This alternative involves implanting a stent-graft in the blood vessel across the aneurysm using conventional catheter-based based placement techniques. The stent-graft treats the aneurysm by sealing the wall of the blood vessel with an impermeable graft material. Thus, the aneurysm is sealed off and the blood flow is kept within the primary passageway of the blood vessel. Increasingly, treatments using stent-grafts are becoming preferred since the procedure results in less trauma and a faster recuperation.

Although stent-grafts are mostly used for treating aneurysms, other medical treatments using stent-grafts are also being explored, and additional applications may be developed in the future. For example, stent-grafts may be used to treat stenosed arteries or other vascular conditions. Stent-grafts may also be used to treat other non-vascular organs, such as the biliary tract. In yet another example, other types of graft materials may be used besides the conventional graft materials that are usually used for aneurysm treatments. While the graft materials that are used for aneurysm treatments are designed to block fluid passage through the graft material, other types of graft materials may be used in stent-grafts, such as small intestine submucosa ("SIS"). As those in the art know, SIS has growth factors that encourage cell migration within the graft material, which eventually results in the migrated cells replacing the graft material with organized tissue.

One current problem with stent-grafts is the way in which the graft material is attached to the stent. The most common way of attaching graft material to a stent is to sew, or suture, the graft material to the stent with thread. However, this process must be done manually by specialists who use special needles to sew thread through the graft material and around the struts of the stent and forceps to knot the thread. As a result, stent-grafts made by this process are expensive and time consuming to make.

In addition, stent-grafts that are made by suturing may suffer from endoleaks once the stent-graft is implanted across an aneurysm. As those in the art know, an endoleak is a blood flow leakage from the lumen of the blood vessel back into the aneurysm. A large amount of leakage after implantation of the stent-graft reduces the effectiveness of the treatment and may leave the patient with a continued risk of rupture despite the treatment. One common source of endoleaks is the perforations through the graft material which are generated by the suturing used to attach the graft material to the stent. In an attempt to overcome the problem of endoleaks, manufacturers of stent-grafts have turned to using especially small diameter needles and thread for the suturing process in order to minimize the size of the perforations. However, this does not completely eliminate the perforations through the graft material and endoleaks through the graft material are still possible. Moreover, this solution increases the cost of stent-grafts even further, since small diameter needles and threads are difficult to work with manually and even require the use of magnifying glasses in some situations.

Another way of attaching graft material to a stent is to sandwich the graft material between an inner stent and an outer stent. In this type of arrangement, opposing pressure from the inner and outer stents squeezes the graft material therebetween. If enough pressure is applied to the graft material by the two stents, the graft material will become immobilized between the stents. However, the known stent-grafts which attempt to sandwich graft material between two stents do not have complimentary features on both stents which cooperate to secure the graft material. Moreover, the known stent-grafts do not orient the two stents together so that cooperative features can secure the stent graft.

Accordingly, it is apparent to the inventor that a stent-graft is desired with cooperative features that secure a graft material to a stent without perforating the graft material. Therefore, a solution is described more fully below that solves these and other problems.

SUMMARY

A stent assembly is provided with a retainer that is installed onto or within a stent. A graft material is disposed between the retainer and the stent. The retainer is oriented relative to the stent so that retaining members on the retainer can cooperate with receiver regions on the stent. As a result, the retainer secures the graft material to the stent without perforating the graft material. Additional details and advantages are described below.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1:
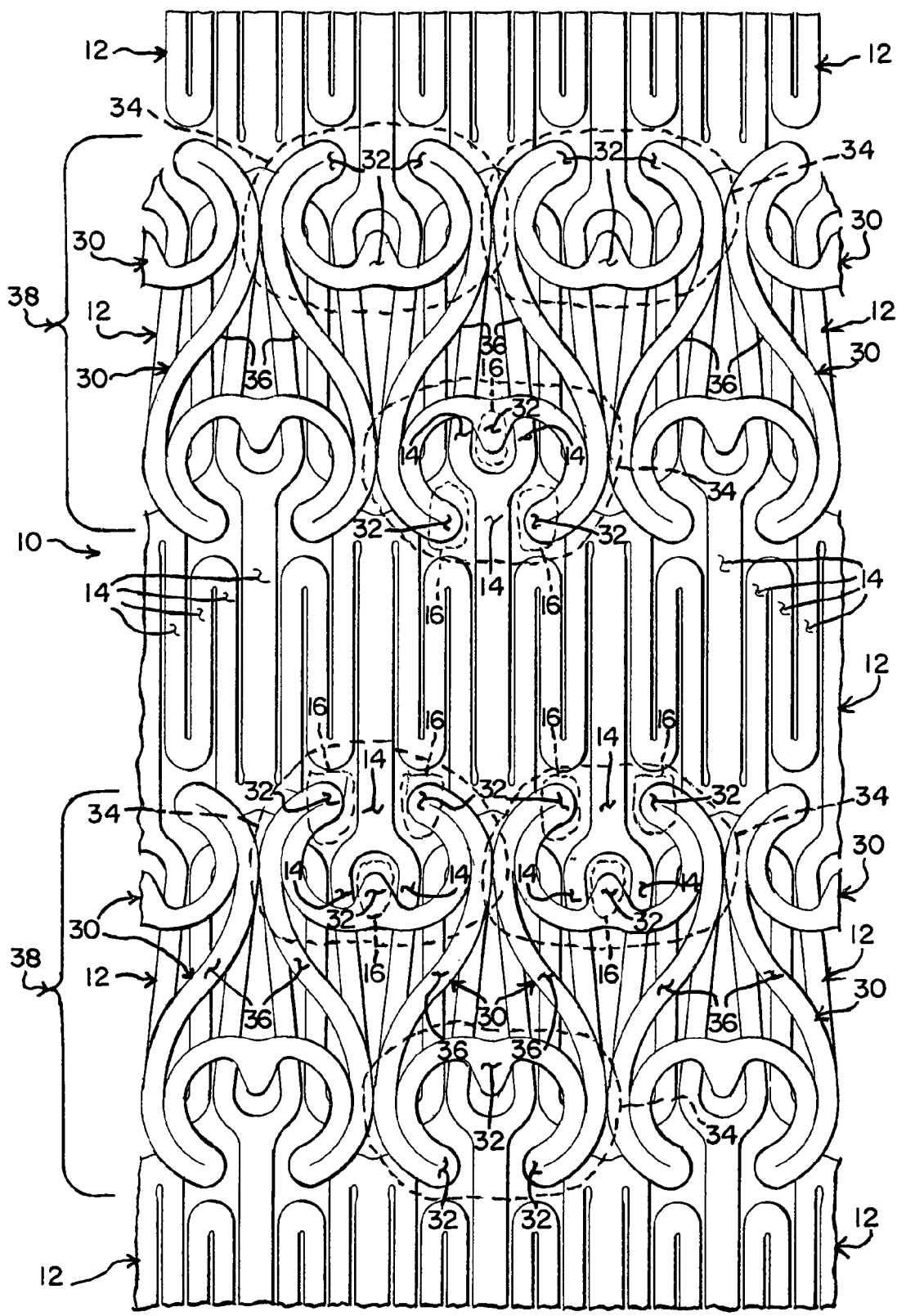
FIG. 1 is a top plan view of a stent assembly, showing a stent and two retainers.

Referring now to the drawings, and particularly to FIGS. 1-5, a stent assembly 10 is shown with a stent 12, a graft material 20, and a retainer 30. As shown, the retainer 30 is disposed on the outside of the stent 12 with the graft material 20 disposed between the stent 12 and the retainer 30. However, other arrangements are also possible, such as disposing the retainer 30 inside of the stent 12 with the graft material 20 disposed therebetween. Generally, the graft material 20 is made of an impermeable material for aneurysm treatments, such as polytetrafluoroethylene ("PTFE") or polyester. However, other materials may also be used depending on the desired treatments, such as small intestine submucosa ("SIS").

Figure 3:
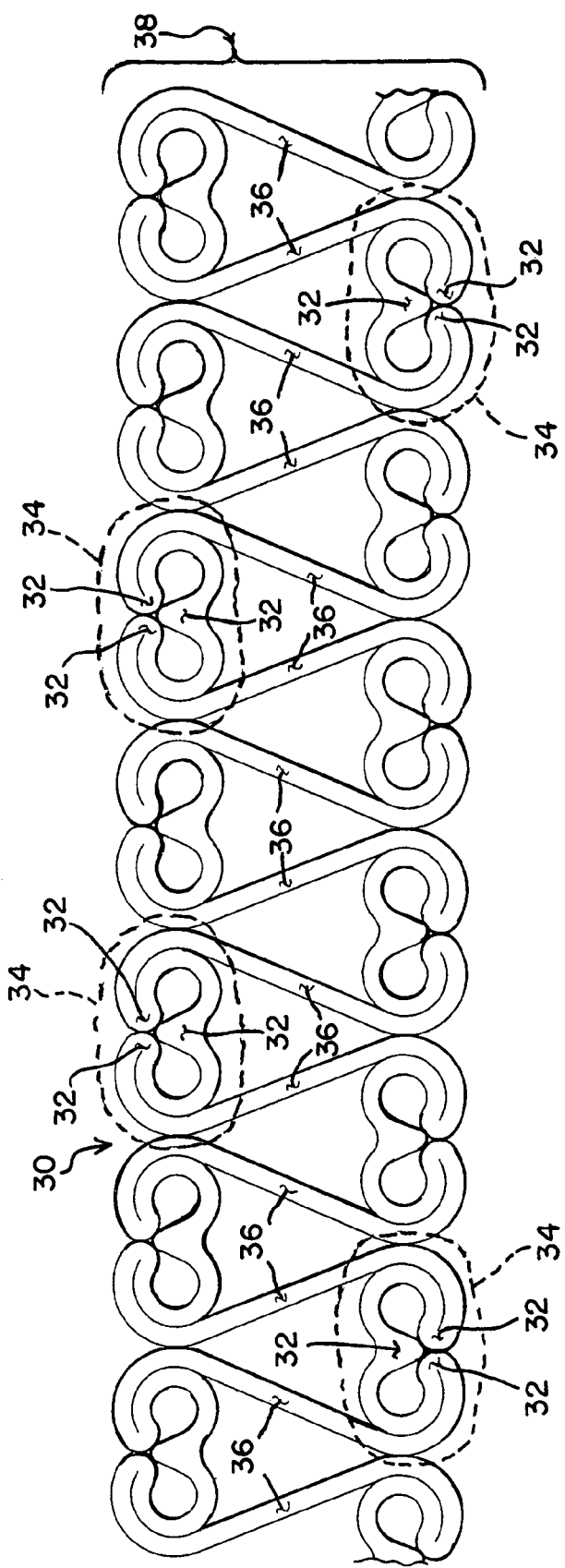
FIG. 3 is a top plan view of the retainer shown in FIG. 1, as it may be laser cut from a metal cannula.
Figure 4:
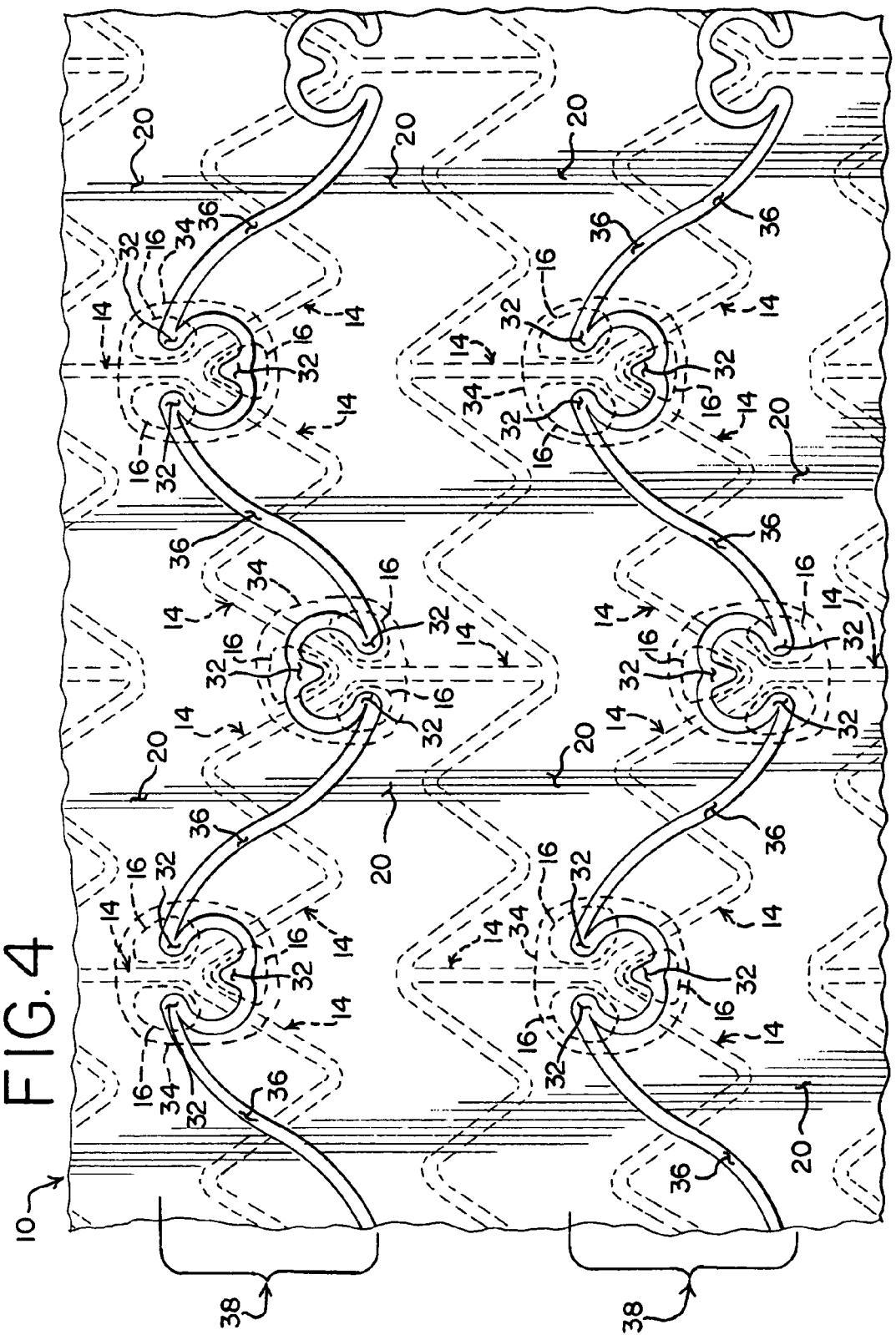
FIG. 4 is a top plan view of the stent assembly shown in FIG. 1, including a graft material, showing the stent assembly expanded.
Figure 5:
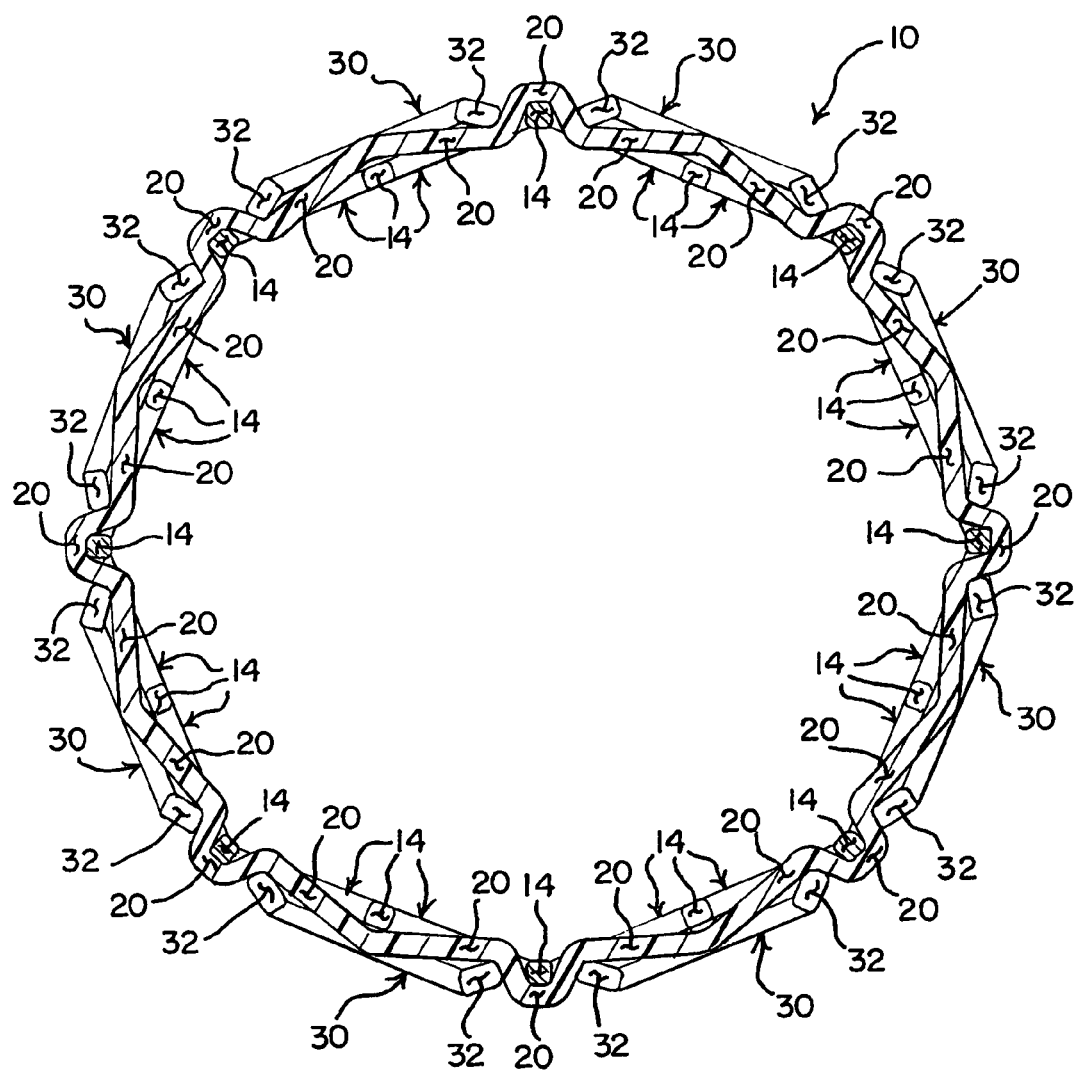
FIG. 5 is a cross sectional view of the stent assembly shown in FIG. 1.

As shown in FIGS. 1, 3 and 4, one embodiment of the retainer 30 consists of single retention bands 38, or bands of retainers, each extending along less than half the axial length of the stent 12. Preferably, each retainer 30 includes a series of retention sites 34 interconnected by connecting struts 36 that extend around the entire outer diameter of the stent 12. However, it is possible that the connecting struts 36 may extend around only a portion of the stent 12 instead of the full diameter. Each of the retention sites 34 includes one or more retaining members 32 that project inward towards the stent 12 (shown in FIG. 5). As shown in the figures, three retaining members 32 are preferably provided at each of the retention sites 34.

Figure 2:
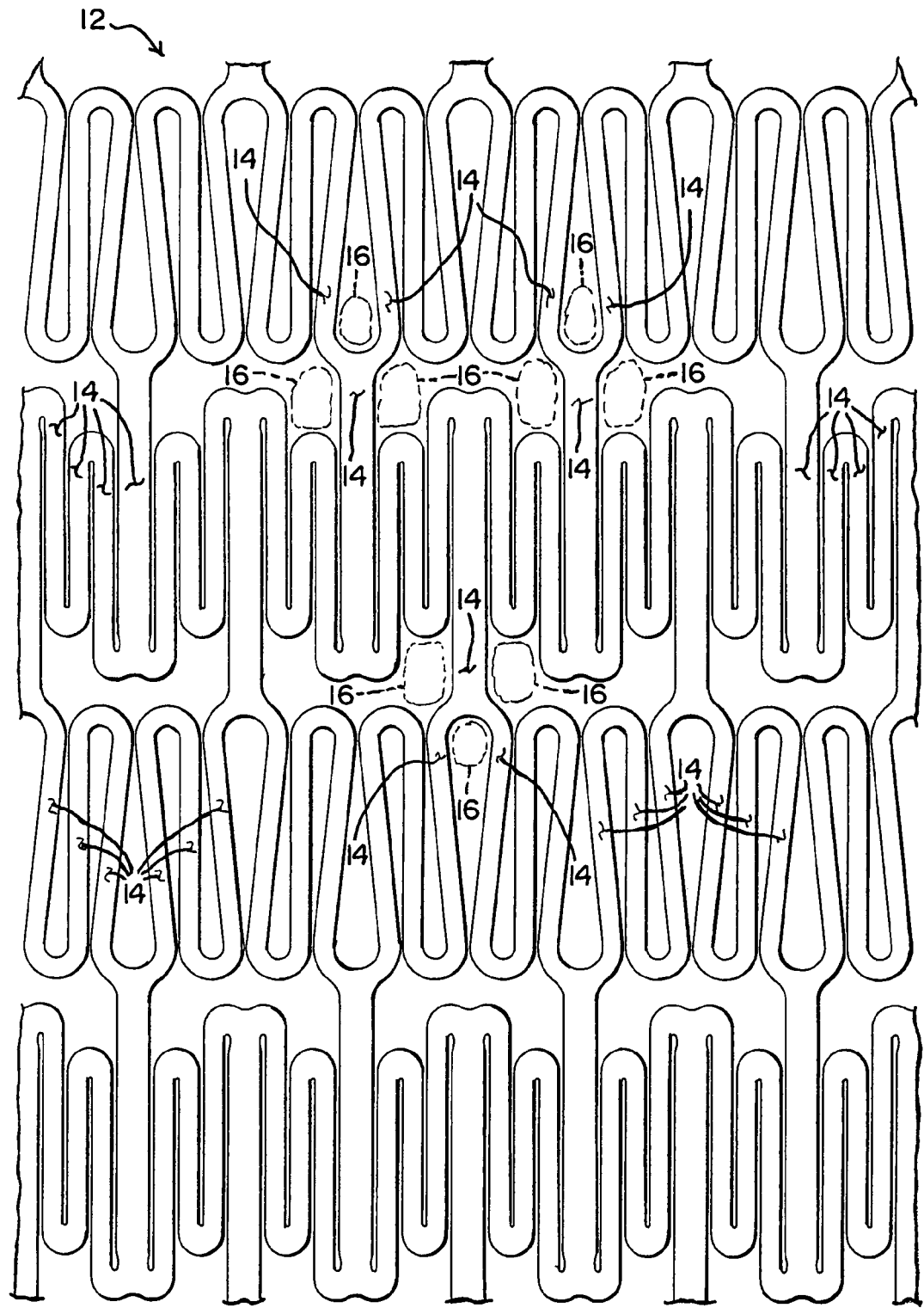
FIG. 2 is a top plan view of the stent shown in FIG. 1.

The stent 12 is also provided with receiver regions 16 that are complimentary with the retaining members 32. As shown in FIGS. 1, 2 and 4, the receiver regions 16 are preferably open regions, or spaces, formed by the stent struts 14. For example, as shown, three receiver regions 16 are formed between the stent struts 14 where the stent struts 14 are joined together in a "Y" connection.

One difference between the stent assembly 10 and prior art stent-grafts is that the retaining members 32 on the retainers 30 and the receiver regions 16 on the stent 12 are formed to be complimentary with each other. Thus, when the retainer 30 and the stent 12 are oriented relative to each other so that the retaining members 32 and the receiver regions 16 align, the retaining members 32 and receiver regions 16 interlock or cooperate with each other. This aspect may be seen in FIGS. 1 and 4, where the retainers 30 are shown on top of an underlying stent 12. In FIG. 1, the retainers 30 and the stent 12 are shown compressed prior to implantation (the graft material 20 is not shown in this figure for clarity). As can be seen, the retainers 30 are radially oriented relative to the stent 12 such that each of the retaining members 32 line up with a complimentary receiver region 16. In FIG. 4, the retainers 30 and stent 12 are shown expanded as the stent assembly 10 would generally look when it is implanted. Like FIG. 1, the retaining members 32 of the retainers 30 line up with the receiver regions 16 of the stent 12. It is also possible that the stent assembly may be arranged with the receiver regions on the retainer and the retaining members on the stent. In this case the retaining members of the stent project towards the retainer and cooperate with the receiver regions on the retainer.

FIGS. 2 and 3 show the stent 12 and one of the retainers 30, respectively, as they may be cut from a cannula. Preferably, the stent 12 and the retainer 30 are laser cut out of metal cannulas using conventional laser cutting technology. The retainer 30 may be made from metals that are currently used to make stents and any other suitable metallic material, such as stainless steel, shape memory metals like nitinol, cobalt-chrome alloys, and amorphous metal alloys. It is also possible that the retainers may be made from non-metallic materials, such as polymers and the like. As shown in FIG. 3, the retainer 30 preferably is made with the retaining members 32 at each retention site 34 closely positioned together. The retaining members 32 are then spread apart as the retainer 30 is installed onto the stent 12, thereby interlocking the retaining members 32 and the receiver regions 16. In the case of balloon expandable stent-graft applications, it is preferable to use a metal with ductile characteristics, such as stainless steel. On the other hand, in the case of self-expandable stent-graft applications, shape memory metals, such as nitinol, are preferable.

Figure 6:
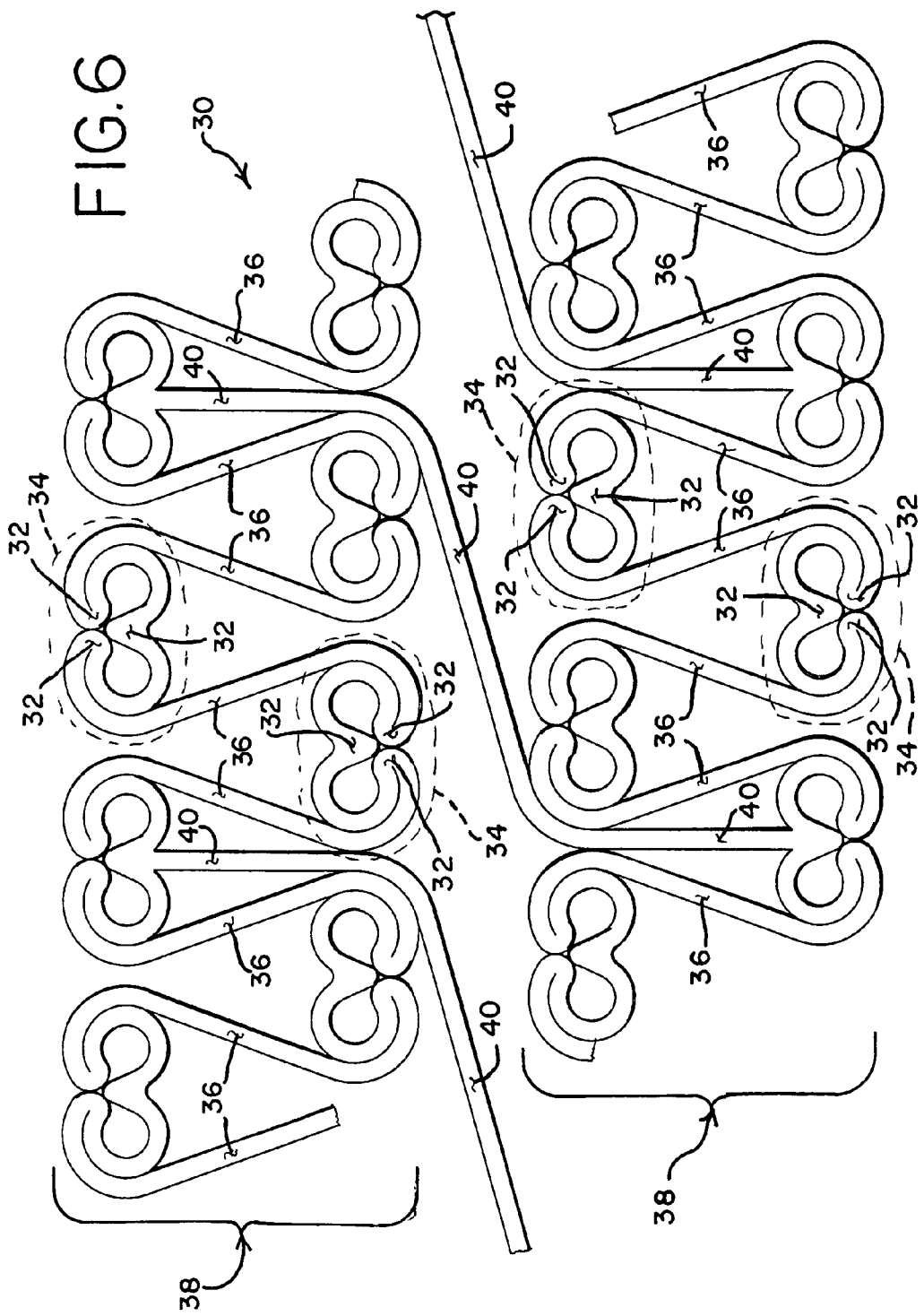
FIG. 6 is a top plan view of a retainer with two retention bands connected with interconnecting struts.
Figure 7:
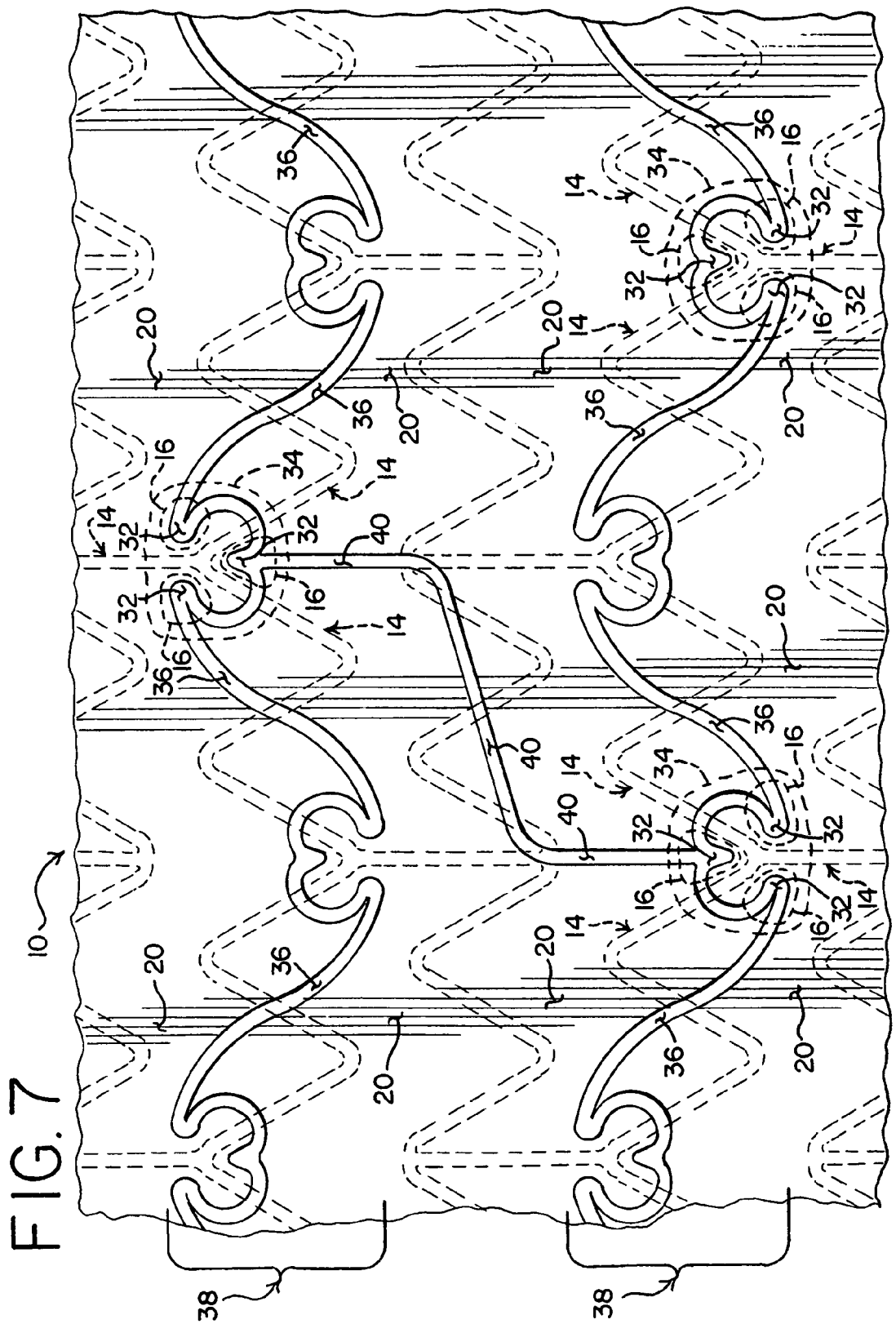
FIG. 7 is a top plan view of a stent assembly, including a stent, a graft material and a retainer, showing the stent assembly expanded, where the retainer includes retention bands connected with interconnecting struts.

Referring now to FIGS. 6 and 7, another embodiment of the retainer 30 is shown. Since most of the details described above apply to this embodiment as well, those details are not repeated. In contrast to the embodiment shown in FIGS. 1, 3 and 4, this embodiment forms one retainer 30 out of several adjacent retention bands 38 that are connected with interconnecting struts 40. Thus, as shown, the interconnecting struts 40 are connected at one end to a retention site 34 of one retention band 38 and are connected at the other end to another retention site 34 on a different retention band 38. The interconnecting struts 40 may be connected to adjacent retention bands 38 at circumferentially offset positions as shown or may also be connected at circumferentially aligned positions. This interconnection may be used to connect only two retention bands 38 as shown or may be repeated to connect numerous retention bands 38.

The advantages of the stent assembly 10 are now apparent. When the retainer 30 is installed onto or within the stent 12, the retaining members 32 on the retainer 30 cooperate with the receiver regions 16 of the stent 12 in order to secure the graft material 20 between the stent 12 and the retainer 30. This is possible because the retaining members 32 are complimentary with the receiver regions 16 and must be oriented to permit the retaining members 32 to cooperate with the receiver regions 16. Thus, unlike traditional sandwiched stent-grafts where a graft material is sandwiched between two stents, the graft material 20 is secured at specific retention sites 34. Therefore, the opposing pressure that may be applied by the retainer 30 and the stent 12 may be reduced compared to traditional sandwiched stent-grafts.

The invention also allows the graft material 20 to be secured to the stent 12 without perforating the graft material 20. In the case of aneurysm treatments, this preserves the impermeable characteristics of the graft material 20. Therefore, endoleaks (which typically reduce the effectiveness of aneurysm treatments) may be eliminated or significantly reduced. This aspect of the invention is possible because the retaining members 32 of the retainer 30 project toward the stent 12, thereby clamping and securing the graft material 20 without actually perforating the graft material 20. In addition, since the graft material 20 is not sutured to the stent 12 like traditional stent-grafts, less labor is needed to manufacture the stent assembly 10. Moreover, because the invention represents a further advancement in the art of minimally invasive endovascular medical treatments, it is possible that fewer patients will need to undergo the risks and long recuperation times of traditional surgeries.

Accordingly, it is now apparent that there are many advantages of the invention provided herein. In addition to the advantages that have been described, it is also possible that there are still other advantages that are not currently recognized but which may become apparent at a later time.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein.

I claim:

1. A stent assembly, comprising:
    an expandable stent adapted for medical implantation, wherein said stent is compressed prior to implantation and is expanded at a site of implantation, said stent comprising a series of three receiver regions, said receiver regions being formed by open regions between three joined stent struts forming a Y-shaped junction;
    a graft material comprising a first surface and a second surface, said first surface and said second surface forming opposite sides of said graft material, wherein said first surface is disposed against at least a portion of said stent;
    a retainer longitudinally aligned with at least a portion of said stent such that said graft is directly sandwiched in a radial direction between said stent and said retainer, said retainer comprising a plurality of retention sites, each retention site comprising three retaining members projecting toward said stent, said retention sites being interconnected by angular connecting struts extending between adjacent retention sites, said retention sites thereby being located at a convergence of two of said angular connecting struts and said retaining members being integral with said angular connecting struts, said retention sites spanning a full diameter of said stent whereby said retention sites and said connecting struts form a band of retainers around said stent; and
    said graft material being secured between said receiver regions of said stent and said retaining members of said retainer, said retainer being oriented relative to said stent to facilitate interlocking engagement between said retaining members and said receiver regions without perforating said graft material, wherein two of said retaining members at said retention sites are located on opposite circumferential sides of one of said three joined stent struts and one of said retaining members at said retention sites is axially displaced from said two retaining members.

2. The stent assembly according to claim 1, wherein said retainer further comprises at least two bands of retainers, said bands being connected by interconnecting struts extending between adjacent bands.

3. The stent assembly according to claim 1, wherein said retainer consists of one band of retainers, said band extending along an axial length of said stent less than half of an entire length of said stent.

4. The stent assembly according to claim 1, wherein said retainer is disposed inside of said stent and said graft material, said graft material being secured between an outer surface of said retainer and an inner surface of said stent.

5. The stent assembly according to claim 1, wherein said retainer is disposed outside of said stent and said graft material, said graft material being secured between an outer surface of said stent and an inner surface of said retainer.

6. The stent assembly according to claim 1, wherein said retainer is metallic.

7. The stent assembly according to claim 6, wherein said retainer is laser cut from a metal cannula.

8. The stent assembly according to claim 7, wherein said retainer is made from a shape memory metallic alloy.

9. The stent assembly according to claim 7, wherein said stent is a balloon expandable stent.

10. The stent assembly according to claim 1, wherein said stent is a self-expanding stent.

11. The stent assembly according to claim 1, wherein said retainer is disposed outside of said stent and said graft material; and said retainer is metallic.

12. The stent assembly according to claim 11, wherein said retainer is made from a shape memory metallic alloy; and said stent is a self-expanding stent.

13. The stent assembly according to claim 11, wherein said retainer is laser cut from a metal cannula; and said stent is a balloon expandable stent.

14. The stent assembly according to claim 1, wherein said retainer is metallic; and said stent is a balloon expandable stent.

15. The stent assembly according to claim 1, wherein said retainer is laser cut from a metal cannula; and said stent is a self-expanding stent.

16. A stent assembly, comprising:
    an expandable stent adapted for medical implantation, wherein said stent is compressed prior to implantation and is expanded at a site of implantation, said stent comprising a series of three receiver regions, said receiver regions being formed by open regions between three joined stent struts forming a Y-shaped junction;
    a graft material comprising a first surface and a second surface, said first surface and said second surface forming opposite sides of said graft material, wherein said first surface is disposed against at least a portion of said stent;
    a retainer longitudinally aligned with at least a portion of said stent such that said graft is directly sandwiched in a radial direction between said stent and said retainer, said retainer comprising a plurality of retention sites, each retention site comprising three retaining members projecting toward said stent, said retention sites being interconnected by connecting struts extending between adjacent retention sites; and
    said graft material being secured between said receiver regions of said stent and said retaining members of said retainer, said retainer being oriented relative to said stent to facilitate interlocking engagement between said retaining members and said receiver regions without perforating said graft material, wherein two of said retaining members at said retention sites are located on opposite circumferential sides of one of said three joined stent struts and one of said retaining members at said retention sites is axially displaced from said two retaining members.

17. The stent assembly according to claim 16, wherein said retaining members are integral with said connecting struts.

18. The stent assembly according to claim 17, wherein said retainer further comprises at least two bands of retainers, said bands being connected by interconnecting struts extending between adjacent bands.

19. The stent assembly according to claim 17, wherein said retainer is disposed outside of said stent and said graft material, said graft material being secured between an outer surface of said stent and an inner surface of said retainer.

20. The stent assembly according to claim 19, wherein said retainer is metallic.

21. The stent assembly according to claim 20, wherein said stent is a self-expanding stent.

22. The stent assembly according to claim 21, wherein said retainer is made from a shape memory metallic alloy.

23. A stent assembly, comprising:
- an expandable stent adapted for medical implantation, wherein said stent is compressed prior to implantation and is expanded at a site of implantation, said stent comprising a plurality of retention sites, each retention site comprising three retaining members projecting toward a retainer, said retention sites being interconnected by connecting struts extending between adjacent retention sites;
- a graft material comprising a first surface and a second surface, said first surface and said second surface forming opposite sides of said graft material, wherein said first surface is disposed against at least a portion of said stent;
- said retainer longitudinally aligned with at least a portion of said stent such that said graft is directly sandwiched in a radial direction between said stent and said stent retainer, said retainer comprising a series of three receiver regions, said receiver regions being formed by open regions between three joined retainer struts forming a Y-shaped junction; and
- said graft material being secured between said receiver regions of said stent and said retaining members of said retainer, said retainer being oriented relative to said stent to facilitate interlocking engagement between said retaining members and said receiver regions without perforating said graft material, wherein two of said retaining members at said retention sites are located on opposite circumferential sides of one of said three joined receiver struts and one of said retaining members at said retention sites is axially displaced from said two retaining members.

* * * * *